United States Patent
Ohno et al.

(10) Patent No.: US 10,268,874 B2
(45) Date of Patent: Apr. 23, 2019

(54) BIOMETRIC AUTHENTICATION APPARATUS AND BIOMETRIC AUTHENTICATION METHOD

(71) Applicant: NEC Corporation, Tokyo (JP)

(72) Inventors: Yuji Ohno, Tokyo (JP); Masahiro Kubo, Tokyo (JP); Katsumi Abe, Tokyo (JP); Takeshi Akagawa, Tokyo (JP); Kimiyasu Takoh, Tokyo (JP); Ersin Altintas, Tokyo (JP); Tetsuri Ariyama, Tokyo (JP)

(73) Assignee: NEC Corporation, Tokyo (JP)

( * ) Notice: Subject to any disclaimer, the term of this patent is extended or adjusted under 35 U.S.C. 154(b) by 8 days.

(21) Appl. No.: 15/523,057

(22) PCT Filed: Oct. 20, 2015

(86) PCT No.: PCT/JP2015/005272
§ 371 (c)(1),
(2) Date: Apr. 28, 2017

(87) PCT Pub. No.: WO2016/067556
PCT Pub. Date: May 6, 2016

(65) Prior Publication Data
US 2017/0337414 A1   Nov. 23, 2017

(30) Foreign Application Priority Data
Oct. 29, 2014  (JP) .................. 2014-219806

(51) Int. Cl.
*G06K 9/00* (2006.01)
*A61B 5/024* (2006.01)
(Continued)

(52) U.S. Cl.
CPC ........ *G06K 9/0012* (2013.01); *A61B 5/02416* (2013.01); *A61B 5/1172* (2013.01);
(Continued)

(58) Field of Classification Search
CPC ............. G06K 9/0012; G06K 9/00087; G06K 9/0002; G06F 17/30256; G06F 21/32;
(Continued)

(56) References Cited

U.S. PATENT DOCUMENTS

| 2008/0175444 A1* | 7/2008 | Maro | G06K 9/00046 382/115 |
| 2010/0008544 A1* | 1/2010 | Abe | G06F 21/32 382/115 |

(Continued)

FOREIGN PATENT DOCUMENTS

| JP | 2001-184490 | 7/2001 |
| JP | 2006-212269 | 8/2006 |

(Continued)

OTHER PUBLICATIONS

International Search Report and Written Opinion dated Jan. 12, 2016, in corresponding PCT International Application.

*Primary Examiner* — Amir Alavi
(74) *Attorney, Agent, or Firm* — Finnegan, Henderson, Farabow, Garrett & Dunner, L.L.P.

(57) ABSTRACT

A biometric authentication apparatus 10 according to the present invention can be installed in facilities such as airports in order to improve the reliability of biometric authentication to ensure a high level of security. The biometric authentication apparatus 10 includes a illumination unit 11 which irradiates a human finger with light; an image acquisition unit 13 which acquires a plurality of images indicating changes in luminance by receiving light scattered at the human finger that is a part of the light with which the human finger is irradiated by the illumination unit 11 and converting the received light to luminance information according to the intensity of the light; an image-to-biometric-information conversion unit 14 which converts the plurality of images acquired by the image acquisition unit 13 to (Continued)

biometric information indicating a pulse wave in the human finger; and a biometric authentication unit 16 which performs biometric authentication when a pulse wave signal which is the biometric information resulting from the conversion by the image-to-biometric-information conversion unit 14 is greater than a predetermined threshold.

8 Claims, 12 Drawing Sheets

(51) Int. Cl.
    *A61B 5/1172*     (2016.01)
    *G01J 3/10*     (2006.01)
    *G01J 3/28*     (2006.01)
    *G06F 17/30*     (2006.01)
    *G06F 21/32*     (2013.01)

(52) U.S. Cl.
    CPC ............... *G01J 3/10* (2013.01); *G01J 3/2823* (2013.01); *G06F 17/30256* (2013.01); *G06F 21/32* (2013.01); *G06K 9/0002* (2013.01); *G06K 9/00013* (2013.01); *G06K 9/00087* (2013.01)

(58) Field of Classification Search
    CPC ....... G01J 3/2823; G01J 3/10; A61B 5/02416; A61B 5/1172
    See application file for complete search history.

(56) References Cited

U.S. PATENT DOCUMENTS

| | | | | |
|---|---|---|---|---|
| 2010/0265040 | A1* | 10/2010 | Kato | G06K 9/00 340/5.83 |
| 2014/0198957 | A1* | 7/2014 | Aoki | G06K 9/00046 382/115 |
| 2014/0241591 | A1* | 8/2014 | Matsuki | G06K 9/00013 382/115 |
| 2016/0256079 | A1* | 9/2016 | Shimano | G06K 9/00013 |
| 2017/0070347 | A1* | 3/2017 | Lutian | H04L 9/3231 |

FOREIGN PATENT DOCUMENTS

| | | |
|---|---|---|
| JP | 2008-67727 | 3/2008 |
| JP | 4468896 | 5/2010 |
| JP | 2014-184002 | 10/2014 |

\* cited by examiner

Fig. 6

| WAVELENGTH (nm) | MEASUREMENT DEPTH (FROM FINGER SURFACE) |
|---|---|
| $\lambda 1$ | 0.1mm |
| $\lambda 2$ | 0.5mm |
| $\lambda 3$ | 2.0mm |

BIOMETRIC AUTHENTICATION APPARATUS AND BIOMETRIC AUTHENTICATION METHOD

CROSS-REFERENCE TO RELATED PATENT APPLICATIONS

This application is a National Stage Entry of International Application No. PCT/JP2015/005272, filed Oct. 20, 2015, which claims priority from Japanese Patent Application No. 2014-219806, filed Oct. 29, 2014. The entire contents of the above-referenced applications are expressly incorporated herein by reference.

TECHNICAL FIELD

The present invention relates to a biometric authentication apparatus and a biometric authentication method for performing biometric authentication, by using biometric information such as fingerprints.

BACKGROUND ART

Biometric identification apparatuses and methods, which use biometric information such as fingerprints for biometric identification, were used only in limited applications such as criminal investigations. However, since the September 11th terrorist attacks in the U.S., biometric identification has been widely introduced in various facilities such as airports as well in order to enhance the security of immigration checks. Problems with biometric authentication apparatuses and methods include measures against fake fingers.

A biometric information measuring apparatus and a biometric information measuring method (a biometric authentication apparatus and a biometric authentication method) that provide protection against fake fingers are described in PTL 1. The technique described in PTL 1 uses ultrasound to measure blood flow rate in conjunction with fingerprint authentication by an imaging unit, thereby determining whether or not a finger is fake.

Another authentication apparatus (a biometric authentication apparatus and a biometric authentication method) that uses biometric information and provides protection against fake fingers is described in PTL 2. The technique described in PTL 2 uses finger blood vessel patterns in conjunction with an image of a finger print to determine whether or not a finger is fake.

CITATION LIST

Patent Literature

PTL 1: Japanese Laid-open Patent Publication No. 2006-212269
PTL 2: Japanese Patent Publication No. 4468896

SUMMARY OF INVENTION

Technical Problem

However, the technique described in PTL 1 has a technical problem that since the technique uses ultrasound, an ultrasonic transmitter and an ultrasonic receiver are required in addition to the imaging unit, which adds to the number of parts. Further, since the technique described in PTL 1 uses ultrasound, the technique may not be able to be used in some environments because of noise typical of ultrasound. Environments where the technique cannot be used may be facilities in which an inverter installed in an air conditioner is used, for example, in which case the frequency of electromagnetic waves generated by the inverter interferes with the frequency of ultrasound. Therefore, the technique described in PTL 1 has the technical problem that the technique can be used only in limited facilities and its installation in wide variety of facilities is difficult.

The technique described in PTL 2 has a technical problem that since authentication using fingerprint images and finger blood vessel patterns cannot determine whether or not a finger is a real living finger, for example, a finger cut from a person different from a person to be authenticated may be authenticated. Therefore, it is difficult for the technique to improve the reliability of biometric authentication.

An object of the present invention is to provide a biometric authentication apparatus and a biometric authentication method that can be introduced in a wide variety of facilities and improve the reliability of biometric authentication to ensure a high level of security.

Solution to Problem

To achieve the object described above, a biometric authentication apparatus according to the present invention includes: a illumination means for irradiating a human finger with light; an image acquisition, means for acquiring a plurality of images indicating changes in luminance by receiving light scattered at the human finger that is a part of the light with which the human finger is irradiated by the illumination means and converting the received light to luminance information according to the intensity of the light; an image-to-biometric-information conversion means for converting the plurality of images acquired by the image acquisition means to biometric information indicating a pulse wave in the human finger; and a biometric authentication means for performing biometric authentication when the amplitude of a pulse wave signal is greater than a predetermined threshold, the pulse wave signal being the biometric information resulting from conversion, by the image-to-biometric-information conversion means.

To achieve the object described above, a biometric authentication method according to the present invention irradiates a human finger with light; when light scattered at the human finger that is a part of the irradiated light is received, converts the received light to luminance information according to the intensity of the light to acquire a plurality of images indicating levels of luminance, converts the plurality of acquired images to biometric information indicating a pulse wave in the human finger, acquires first reliability information indicating the reliability of biometric authentication on the basis of the biometric information resulting from, the conversion, and performs biometric authentication depending on a reliability result indicated by the acquired first reliability information.

Advantageous Effects of Invention

The present invention can be introduced in a wide variety of facilities and improves the reliability of biometric authentication to ensure a high level of security.

BRIEF DESCRIPTION OF DRAWINGS

FIG. 6 is a table illustrating depths to which light rays of different wavelengths penetrate.

DESCRIPTION OF EMBODIMENTS

Exemplary embodiments of the present invention will be described below with reference to the drawings.

First Exemplary Embodiment

Figure 1:
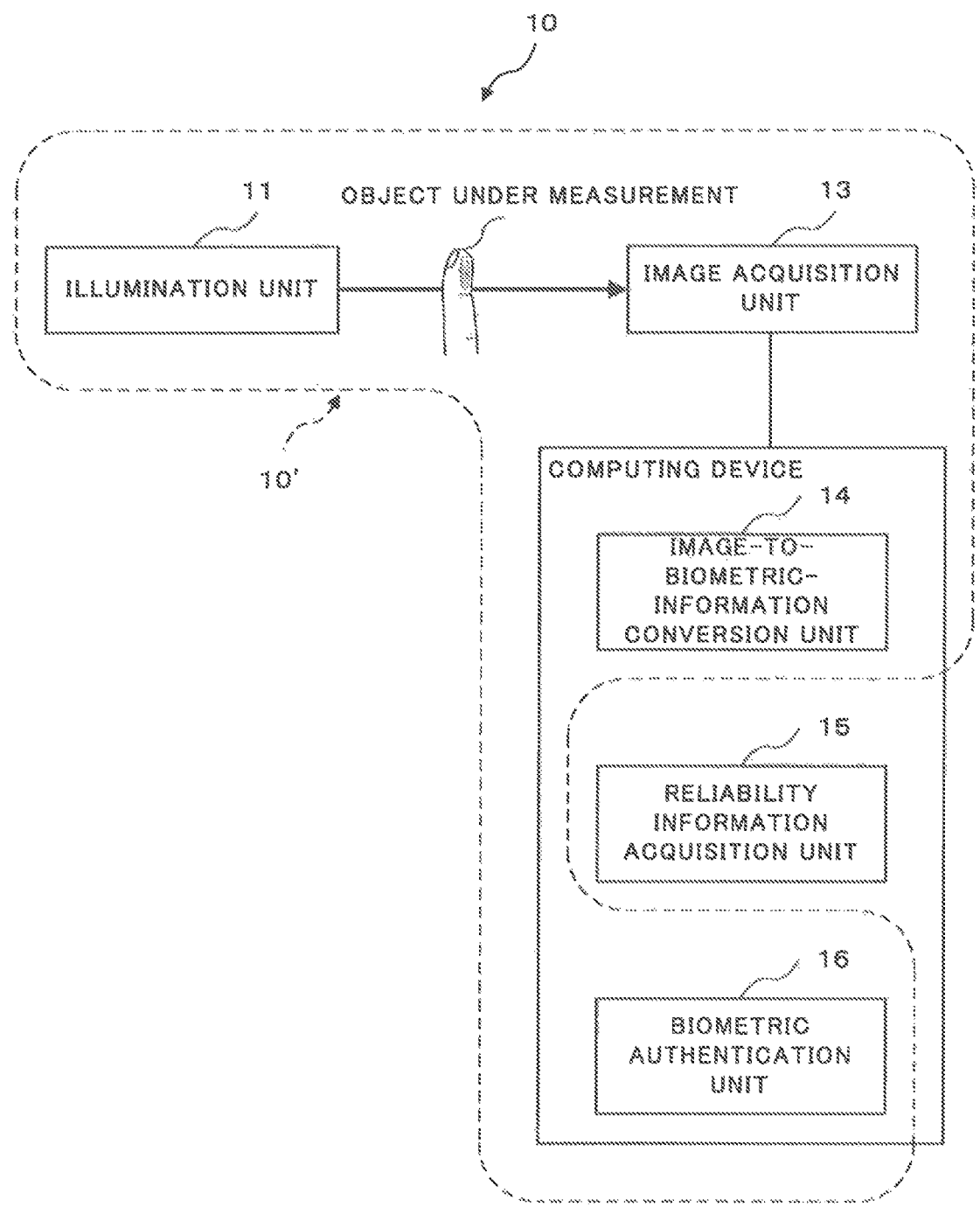
FIG. 1 is a configuration diagram illustrating a configuration of a biometric authentication apparatus according to one exemplary embodiment (a first exemplary embodiment) of the present invention.
Figure 2:
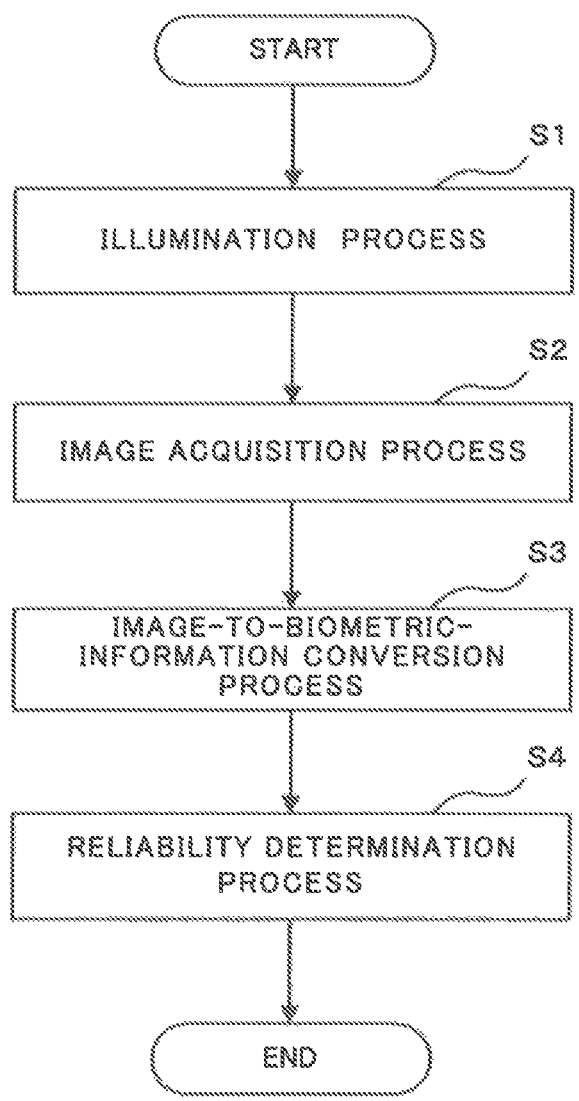
FIG. 2 is a flowchart of a process performed by the biometric authentication apparatus according to one exemplary embodiment (the first exemplary embodiment) of the present invention.

One exemplary embodiment (a first exemplary embodiment) of the present invention will be described with reference to FIGS. 1 and 2. First, a configuration of a biometric authentication apparatus 10 according to the present exemplary embodiment will be described with reference to FIG. 1. FIG. 1 is a configuration diagram illustrating a configuration of the biometric authentication apparatus 10 according to the present exemplary embodiment (the first exemplary embodiment).

The biometric authentication apparatus 10 according to the present exemplary embodiment includes a illumination unit (illumination means) 11, an image acquisition unit (image acquisition means) 13, an image-to-biometric-information conversion unit (image-to-biometric-information conversion means) 14, a reliability information acquisition unit (reliability information acquisition means) 15, and a biometric authentication unit (biometric authentication means) 16.

The illumination unit 11 irradiates a human finger with light of a designed wavelength. When a human finger is irradiated with light, the light irradiated from the illumination unit 11 is scattered at the human finger to produce scattered light. The intensity of the scattered light varies depending on designed wavelengths because the absorbance of light irradiated from the illumination unit 11 differs from one human finger to another. It is assumed in the present exemplary embodiment that the illumination unit 11 irradiates a human finger with light rays of different wavelengths in the range from a visible light region to a near infrared light region. The visible light region is a wavelength region from about 380 nm to about 780 nm and the near infrared light region is a wavelength region from about 700 nm to about 2500 nm.

The image acquisition unit 13 receives light scattered by a human finger. The image acquisition unit 13 converts the received light to an electrical signal according to the intensities of the received light and acquires a plurality of images (image information A) in a set period of time. At this time point, the image acquisition unit 13 acquires image information at each of the wavelengths of light irradiated from the illumination unit 11.

The image-to-biometric-information conversion unit 14 converts image information A acquired by the image acquisition unit 13 to biometric information representing a pulse wave in a human finger. The reliability information acquisition unit 15 acquires reliability information representing the reliability of biometric authentication on the basis of biometric information resulting from conversion by the image-to-biometric-information conversion unit 14. The biometric authentication unit 16 determines whether biometric authentication is reliable on the basis of reliability information acquired by the reliability information acquisition unit 15.

A method for acquiring reliability information by the reliability information acquisition unit 15 will now be illustrated. The reliability information acquisition unit 15 refers to biometric information resulting from conversion by the image-to-biometric-information conversion unit 14 and, when the amplitude of a pulse wave signal is smaller than a predetermined amplitude which is a predetermined threshold, or when the amplitude of a pulse wave signal cannot be found, the reliability information acquisition unit 15 determines that no pulse wave is present in the finger and that the finger is not a finger of the person to be authenticated but a finger cut from another person or a fake finger. In response to this determination, the biometric authentication unit 16 avoids automatically performing biometric authentication in the case of the finger cut from a person or fake finger, for example, but instead notifies that the finger may be a finger cut from a person or a fake finger.

In this way, the present exemplary embodiment is made up of optical devices alone, the illumination unit 11 irradiates a human finger with light, and the image acquisition unit 13 acquires a plurality of images at different wavelengths of illumination light. Therefore, the present exemplary embodiment does not need to consider interference between the frequency of ultrasound, for example, and the frequency of electromagnetic waves generated by an inverter installed in an air conditioner or the like and can be introduced in a wide variety of facilities.

Further, in the present exemplary embodiment, reliability information is acquired on the basis of biometric information, determination is made as to whether biometric authentication is reliable on the basis of the acquired reliability information, and thus it may be determined, for example, that a finger does not belong to a person to be authenticated but is a finger cut from another person. According to the present embodiment, this prevents biometric authentication of a finger cut from a person or the like from being automatically performed, thereby improving the reliability of the biometric authentication. Thus, the present exemplary embodiment can be introduced in a wide variety of facilities and improve the reliability of biometric authentication to ensure a high level of security, as described above.

(Process Performed by the Biometric Authentication Apparatus 10)

A process performed by the biometric authentication apparatus 10 according to the present exemplary embodiment will be described next with reference to FIG. 2. FIG. 2 is a flowchart of a process performed by the biometric authentication apparatus 10 according to the present exemplary embodiment (the first exemplary embodiment).

In step S1, the biometric authentication apparatus 10 performs a illumination process. In this process, the illumination unit 11 of the biometric authentication apparatus 10 irradiates a human finger with light of a designed wavelength. In this case, the illumination unit 11 irradiates the human finger with light rays of a plurality of wavelengths in the range from a visible light region to a near infrared region.

In step S2, the biometric authentication apparatus 10 performs an image acquisition process, in this process, the image acquisition unit 13 of the biometric authentication apparatus 10 receives light scattered at the human finger. The image acquisition unit 13 then converts the received light to an electrical signal according to the intensities of the received light and acquires a plurality of images (image information A) in a set period of time. In this case, the image acquisition unit 13 acquires pieces of image information A at the wavelengths of light irradiated from the illumination unit 11.

In step S3, the biometric authentication apparatus 10 performs a biometric information conversion process. In this process, the biometric authentication apparatus 10 performs processing for converting the acquired image information A to biometric information that represents a human pulse wave.

In step S4, the biometric authentication apparatus 10 performs a reliability determination process. In this process, the reliability information acquisition unit 15 of the biometric authentication apparatus 10 acquires reliability information indicating the reliability of biometric authentication on the basis of a pulse wave signal which is the biometric information representing the human pulse wave resulting from the conversion in step S3 and determines, on the basis of the acquired reliability information, whether to perform biometric authentication. In an example of the method for acquiring the reliability information by the reliability information acquisition unit 15, the reliability information acquisition unit 15 refers to the biometric information resulting from the conversion by the image-to-biometric-information conversion unit 14 and, if the amplitude of the pulse wave signal is smaller than a predetermined amplitude, or if no pulse wave signal amplitude can be found, the information acquisition unit 15 determines that no pulse wave is being emitted from the finger. When the information acquisition unit 15 determines that no pulse wave is in the finger, the information acquisition unit 15 determines that the finger is not a finger of the person to be authenticated but a finger cut from another person or a fake finger. In response to the determination, the biometric authentication unit 16 avoids automatically performing biometric authentication in the case of the finger cut from a person or fake finger, for example, and notifies that the finger can be a finger cut from another person or a fake finger. Note that the amplitude of a pulse wave signal is smaller than the predetermined amplitude if the maximum amplitude of the pulse wave signal with a period in the range from 0.4 s to 2 s (a frequency in the range from 0.5 Hz to 2.5 Hz) is smaller than the maximum amplitude of a pulse wave signal with a period less than or equal to 0.4 s (a frequency higher than or equal to 2.5 Hz). No amplitude of a pulse wave signal can be found if the maximum amplitude of the pulse wave signal with a period in the range of 0.4 s to 2 s (a frequency in the range of 0.5 Hz to 2.5 Hz) is smaller than the average amplitude of pulse wave signals.

In this way, the present exemplary embodiment uses only optical devices in conversion to biometric information: the illumination unit 11 irradiates a human finger with light and the image acquisition unit 13 acquires a plurality of images at different wavelengths of illumination light. Therefore, the present exemplary embodiment does not need to consider interference between the frequencies of ultrasound, for example, and the frequency of electromagnetic waves generated by an inverter installed in an air conditioner or the like and therefore can be introduced in a wide variety of facilities.

Further, in the present exemplary embodiment, reliability information is acquired on the basis of biometric information, determination is made as to whether biometric authentication is reliable on the basis of the acquired reliability information, and thus it may be determined, for example, that a finger does not belong to a person to be authenticated but is a finger cut from another person. According to the present embodiment, this prevents biometric authentication of a finger cut from a person or the like from being performed, thereby improving the reliability of the biometric authentication. Thus, the present exemplary embodiment can improve the reliability of biometric authentication to ensure a high level of security.

Second Exemplary Embodiment

Figure 3:
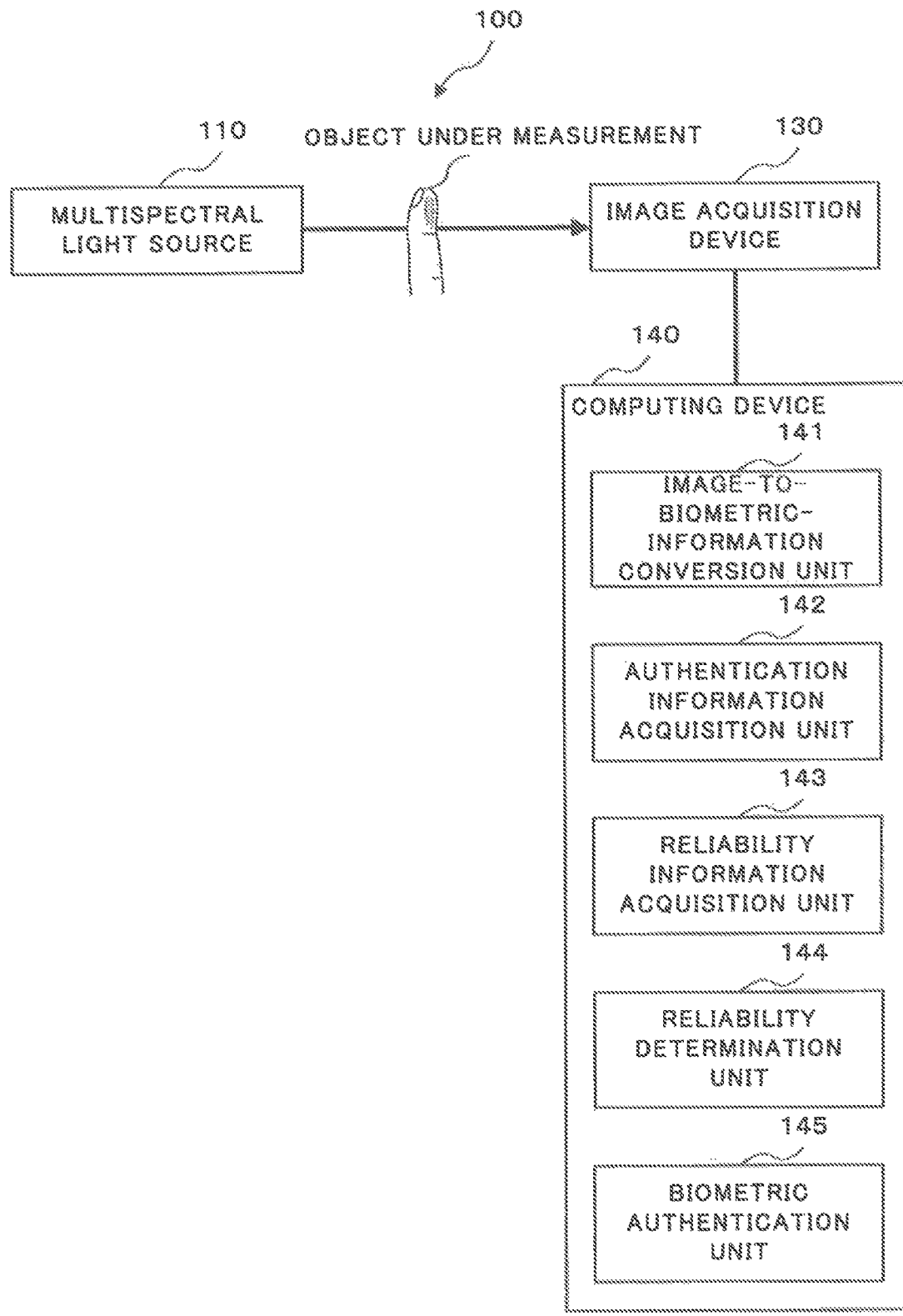
FIG. 3 is a configuration diagram illustrating a configuration of a biometric authentication apparatus according to an alternative exemplary embodiment (a second exemplary embodiment) of the present invention.

An alternative exemplary embodiment (a second exemplary embodiment) of the present invention will be described with reference to FIGS. 3 to 13. First, a configuration of a biometric authentication apparatus 100 according to the present exemplary embodiment will be described with reference to FIG. 3. FIG. 3 is a configuration diagram illustrating a configuration of the biometric authentication apparatus 100 according to the present exemplary embodiment (the second exemplary embodiment).

As illustrated in FIG. 3, the biometric authentication apparatus 100 according to the present exemplary embodiment includes a multispectral light source (illumination means) 110, an image acquisition device (image acquisition means) 130 and a computing device 140.

The multispectral light source 110 is a light source capable of switching between different wavelengths and irradiates a human finger with light. Examples of light sources capable of switching between different wavelengths include multiple monochromatic LEDs, multiple monochromatic lasers, a wavelength-variable laser and a variable multi-wavelength light source. The wavelengths here are any of wavelengths in the range from a visible light region to a near infrared light region. The visible light region is a wavelength region from about 380 nm to about 780 nm and the near infrared light region is a wavelength region from about 700 nm to about 2500 nm. "LED" is an abbreviation for "Light Emitting Diode".

The multispectral light source 110 in the present exemplary embodiment includes a switching unit, not depicted, capable of switching between different wavelengths. The switching unit switches between different wavelengths to use in such a manner that the multispectral light source 110 continuously irradiates a human finger with light of different wavelengths. For example, the multispectral light source 110 switches from light of a wavelength λ1 (for example a visible light wavelength of 500 nm) to light of another wavelength λ2 (for example a visible light wavelength of 600 nm) to light of yet another wavelength λ3 (for example a near-infrared wavelength of 750 nm) with a period of 1 kHz while irradiating for a predetermined period of time (for example 2 seconds). In another example, after irradiating with light of a wavelength λ3 for a predetermined period of time (for example 1 second), switching is made to another wavelength λ1 and illumination is performed, then further switching is made to another wavelength λ2 and illumination is performed. While examples in which switching is made among three wavelengths have been given above, switching between two wavelengths or four or more wavelengths may be performed in a like manner.

Monochromatic LED, monochromatic laser, wavelength-variable laser and variable multi-wavelength light source technologies are well known and therefore detailed descriptions of the monochromatic LEDs, monochromatic lasers, wavelength-variable lasers and variable multi-wavelength light sources will be omitted.

The image acquisition device 130 is a device capable of acquiring two-dimensional image information. The image acquisition device 130 may be a CCD image sensor, for example. The image acquisition device 130 acquires image information A on the basis of scattered light originating from a human finger. The image information A is a plurality of images taken during a set period of time. Note that a method for acquiring the image information A is well known and therefore will be only briefly described and detailed description will be omitted. First, when a human finger is irradiated with light from the multispectral light source 110, the image acquisition device 130 receives light scattered at the human finger. The image acquisition device 130 then converts the received light to an electrical signal according to the intensity of the received light to acquire image information A. In the present exemplary embodiment, pieces of image information A1 to A3 at different wavelengths of the multispectral light source 110 are acquired as the image information A. The pieces of image information A1 to A3 will be described later with reference to FIG. 4. While an example that uses three pieces of image information at different wavelengths will be described here, two or more pieces of image information at different wavelengths may be acquired. More preferably, more pieces of image information at different wavelengths are acquired.

While the image acquisition device 130 in the present exemplary embodiment is a CCD image sensor as state above as state above, the image acquisition device 130 is not limited to this. The image acquisition device 130 may be any device that can capture images of scattered light from a human finger, such as a CMOS image sensor, an InGaAS camera, for example, which are well-known technologies, "CCD" is an abbreviation for "Charge Coupled Device". "CMOS" is an abbreviation for "Complementary Metal Oxide Semiconductor".

Figure 4:
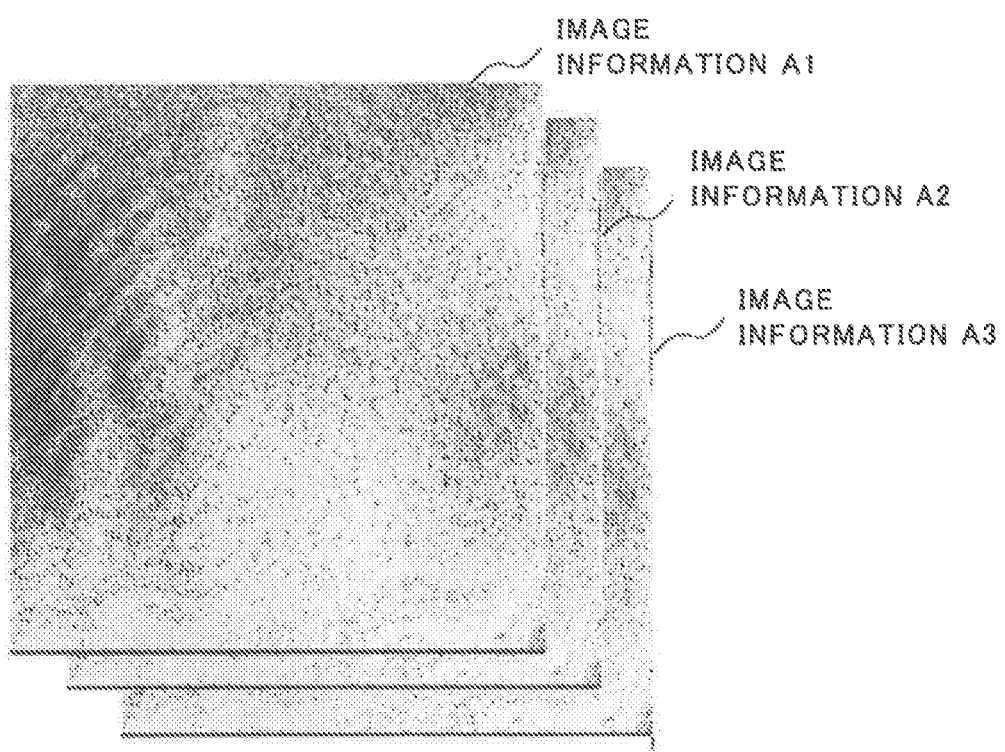
FIG. 4 is a diagram illustrating an example of image information A.

The image information A will be described with reference to FIG. 4 first. FIG. 4 is a diagram illustrating one example of the image information A. Image information A1 its the present exemplary embodiment represents image information acquired by the image acquisition device 130 while a human finger is irradiated with light of a wavelength λ1 (500 nm) in the visible light range by the multispectral light source 110 for a predetermined period of time. Image information A2 represents image information acquired by the image acquisition device 130 while the human finger is irradiated with light of another wavelength λ2 (600 nm) in the visible light range by the multispectral light source 110 for a predetermined period of time. Image information A3 represents image information acquired by the image acquisition device 130 while the human finger is irradiated with light of a wavelength λ3 (750 nm) in the near infrared range by the multispectral light source 110 for a predetermined period of time. Returning to FIG. 3, the description of the configuration of the biometric authentication apparatus 100 will be continued.

The computing device 140 includes an image-to-biometric-information conversion unit (image-to-biometric-information conversion means) 141, a reliability information acquisition unit (reliability information acquisition means) 143 and a reliability determination unit (reliability determination means) 144.

The image-to-biometric-information conversion unit 141 performs a process for converting image information A acquired by the image acquisition device 130 to biometric information C. The biometric information C may be first to third pieces of biometric information C1 to C3, for example; the first biometric information C1 may be a fingerprint image of a surficial part of a human finger; the second biometric information C2 may be a fingerprint information of an inner part of the human finger; and the third biometric information may be a pulse wave signal originating from a human pulse wave.

The image-to-biometric-information conversion unit 141 converts image information A to biometric information C. When converting, the image-to-biometric-information conversion unit 141 uses information illustrated in FIG. 5 or 6 to determine which image information A out of pieces of image information A1 to A3 is to be used and how to compute to convert the image information to first to third pieces of biometric information C1 to C3.

Therefore, before describing the first to third pieces of biometric information C1 to C3, information indicating which piece of image information A is to be used and how to compute to convert the piece of image information A to biometric information C will be described first with reference to FIGS. 5 and 6.

Figure 5:
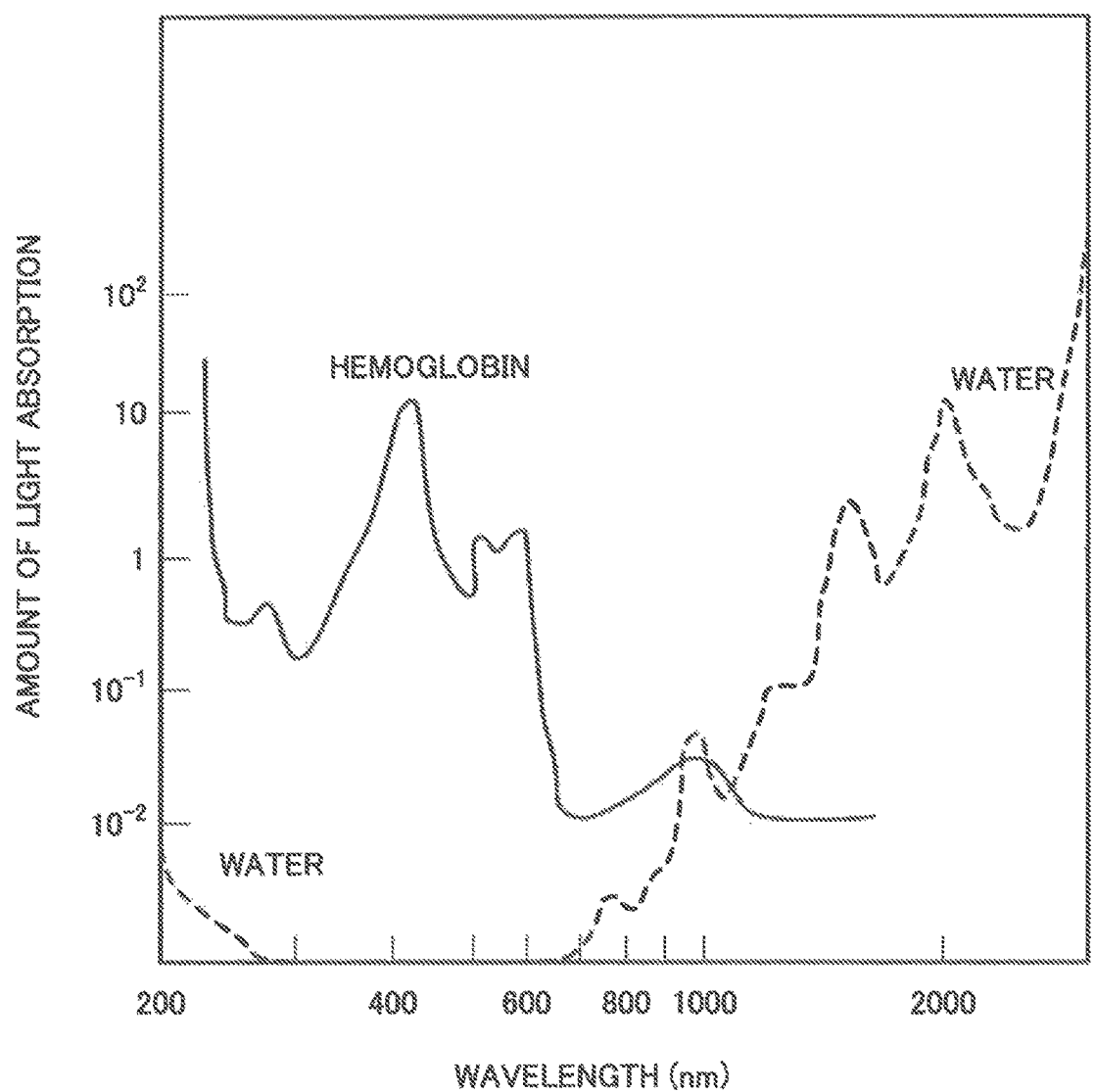
FIG. 5 is a diagram illustrating spectrum information B concerning a living body.

FIG. 5 illustrates wavelength characteristics of amounts of light absorbed in water and hemoglobin in a living body as spectral information B concerning the living body. By using FIG. 5, the image-to-biometric-information conversion unit 141, which will be described later, can know which of the pieces of image information at different wavelengths indicates a large amount of absorption of light passing through a living body. Accordingly, when the image-to-biometric-information conversion unit 141 is to acquire image information indicating a large amount of absorption of light passing through a living body or to acquire image information indicating a small amount of absorption of light passing through a living body, the image-to-biometric-information conversion unit 141 can identify which of the pieces of image information at different wavelengths is to be used. When the image-to-biometric-information conversion unit 141 is to acquire biometric information about a deep part of a living body, the image-to-biometric-information conversion unit 141 preferably uses image information representing a small amount of absorption of light passing through the living body, i.e. image information based on a wavelength λ3 (750 nm) which indicates a small amount of absorption of light in hemoglobin. When converting to the third biometric information C3 about a deep part of the living body, most accurate information can be acquired by using image information based on a wavelength around the wavelength λ3 (750 nm).

While spectral information B in the present exemplary embodiment is the amounts of absorption of light in hemoglobin and water, the spectral information B is not limited to the amounts of light absorption in hemoglobin and water. Other substances that are found in human fingers and absorb different amounts of light depending on wavelengths, such as melanin and carotene, may be used. Further, scattering characteristics that are dependent on constituents and structures may be included in the spectral information B. As the spectral information B, typical spectral information concerning a group to be authenticated may be used or spectral information concerning an individual or group to be authenticated may be acquired in advance.

FIG. 6 illustrates example depths to which light rays of different wavelengths penetrate. As illustrated in FIG. 6, when a human body is irradiated with light of a wavelength λ1 (500 nm), for example, light scattered up to a depth of about 0.1 mm from the surface will be observed. By using FIG. 6, the image-to-biometric-information conversion unit 141, which will be described later, can know which of pieces of image information based on different wavelengths is to be used to acquire, for example, first biometric information C1 about a surficial part of a finger. Thus, the image-to-biometric-information conversion unit 141 can choose and convert the image information of λ1 to first biometric information C1. In this example, when converting to first biometric information C1, which is a fingerprint image of a surficial part of a human finger, the image-to-biometric-information conversion unit 141 converts image information A1 acquired during illumination with light of λ1. When converting to second biometric information C2, which is a fingerprint image of an inner part of the human finger, the image-to-biometric-information conversion unit 141 uses image information based on a wavelength at which the amount of absorption of light passing through the living body is small in the spectral information B. In the present exemplary embodiment, image information A2 acquired during illumination with light of a wavelength λ2 (600 nm) and image information A3 acquired during illumination with light of a wavelength λ3 (750 nm) are used. In addition, biometric information C1 may also be used as appropriate. When converting to third biometric information C3, which represents a human pulse wave, the image-to-biometric-information conversion unit 141 uses one or more of pieces of image information A1 to A3 for conversion. Note that more exact numerical values than the values in FIG. 6 can be calculated from spectral information B.

As described above, in the present exemplary embodiment. FIG. 5 or 6 is used to determine which of pieces of image information based on different wavelengths can be converted to biometric information at a certain depth from the surface of a human finger and to determine how much light is absorbed in a substance in a human finger at the wavelength.

Figure 7:
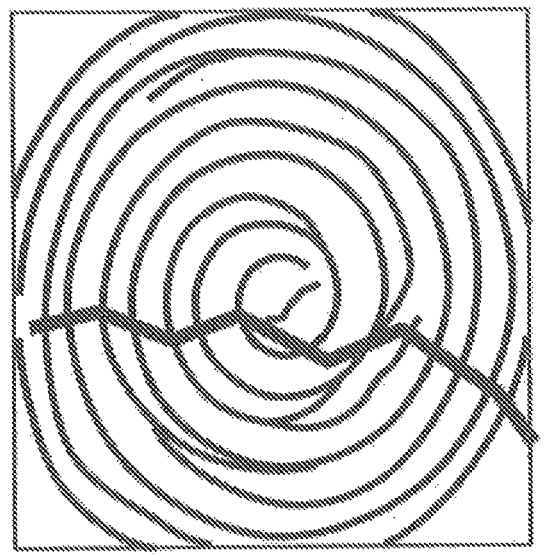
FIG. 7 is a diagram illustrating first biometric information C1.

First biometric information C1 illustrated in FIG. 7 will be described. As noted above, the first biometric information C1 is a fingerprint image of a surficial part of a human finger. While processes such as noise removal, binarization and thinning are performed during conversion from image information A to first biometric information C in the present exemplary embodiment, these are well-known techniques and therefore description thereof will be omitted. As stated above, in the first biometric information C1, a fingerprint image of a surficial part of a human finger is represented by using image information that indicates a large amount of absorption of light passing through a living body in spectral information B. Accordingly, if soil or the like is attached to a human finger, an image of the attached soil or the like is indicated in the first biometric information C1.

Figure 8:
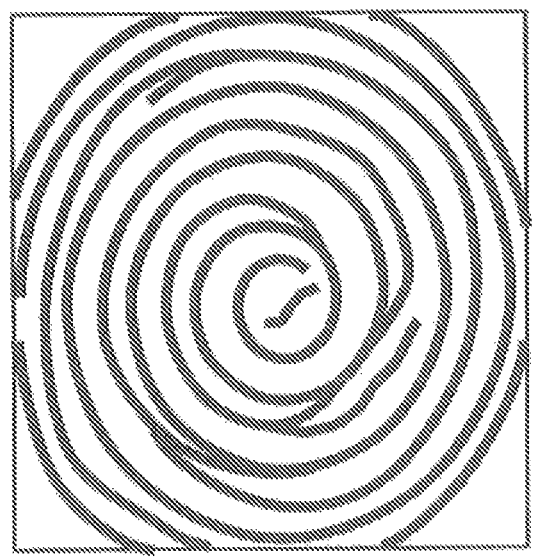
FIG. 8 is a diagram illustrating second biometric information C2.

Second biometric information C2 illustrated in FIG. 8 will be described. As stated above, the second biometric information C2 is a fingerprint image of an inner part of a human finger. To calculate the second biometric information C2, pieces of image information that indicate small amounts of absorption of light passing through a living body in spectral information B (for example, pieces of image information A2 and A3) out of image information A are used. By using the image information A2 and A3, spectral information B, and biometric information C1, biometric information about an inner part of the human finger in the depth direction is calculated. In this way, biometric information C2 about a part at a particular depth can be calculated.

As stated above, the second biometric information C2 represents a fingerprint image of an inner part of a human finger at a particular depth. Therefore, even if soil is attached to the surface of the human finger, for example, the second biometric information C2, unlike the first biometric information C1, indicates no image of the attached soil. When the first biometric information C1 and the second biometric information C2 are superimposed on one another, the portion of the first biometric information C1 in which the attached soil appears and the corresponding portion of the second biometric information C2 do not correlate with each, other, i.e. the degree of correlation between the first biometric information C1 and the second biometric information C2 in the portion is low, as will be described later. More specifically, the value of a cross-correlation function between the obscure portion of the biometric information C1 in which the attached soil appears and the corresponding portion of the biometric information C2 is lower than a given value whereas the values of the cross-correlation function between the biometric information C1 and the biometric information C2 in the other portions are higher than the given value. A value of the cross-correlation function is lower than a given value if the correlation value is lower than or equal to about 0.3 and a value of the cross-correlation function is higher than the given value if the value is higher than or equal to about 0.7. Preferably, determination as to whether a value of the cross-correlation function is high or low is made as appropriate by taking into consideration an object under measurement and a measurement environment. Thus, the presence of soil or the like on the surface of a finger can be detected by using the first biometric information C1 and the second biometric information C2.

Further, a fingerprint image of a surficial part of a human finger is indicated in the first biometric information C1 as stated above. Therefore, if a fingerprint of a third person is attached to a finger, a fingerprint image of the third person is indicated in the first biometric information. In the second biometric information C2, in contrast, a fingerprint image of an inner portion of a human finger at a particular depth is indicated as described above. Accordingly, a fingerprint image of a person under measurement, rather than a fingerprint image of a third person, is indicated in the second biometric information C2. Thus, when the first biometric information C1 and the second biometric information C2 are superimposed on one another, there is no correlation between the first biometric information C1 and the second biometric information C2, i.e. the degree of correlation between the first biometric information C1 and the second biometric information C2 is low, as will be described later. More specifically, a value of the cross-correlation function between the biometric information C1 and the biometric information C2 is lower than a given value. A value of the cross-correlation function is lower than a given value if the correlation value is lower than or equal to about 0.3. Thus, a fraud such as an attached fingerprint of a third person can be detected by using the first biometric information C1 and the second biometric information C2.

While the first biometric information C1 and the second biometric information C2 are used to acquire authentication information E in the present exemplary embodiment as will be described later, a part of the first biometric information C1 and the second biometric information C2 or only the second biometric information C2 may be used to acquire authentication information E. However, preferably the first biometric information C1 and the second biometric information C2 are used because the second biometric information C2 is likely to indicate fainter fingerprint patterns than the first biometric information C1 and, if only the second biometric information C2 is used to acquire authentication information E, it is difficult to extract feature points.

Figure 9:
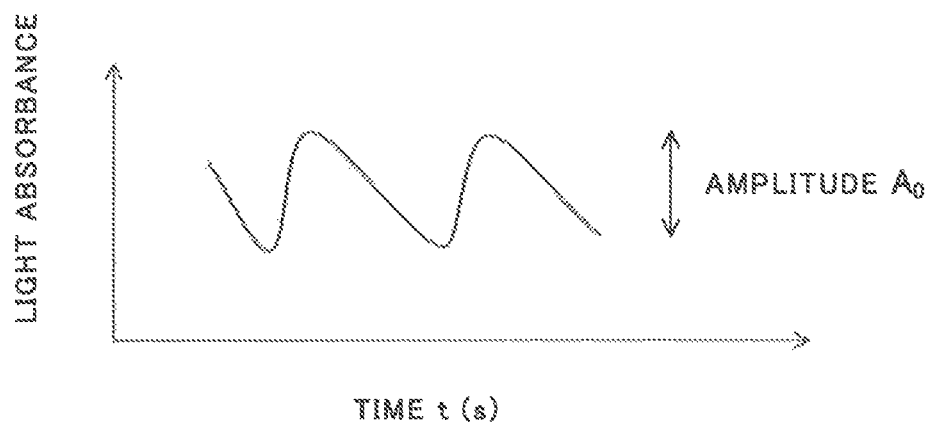
FIG. 9 is a diagram illustrating third biometric information C3.

Third biometric information C3 will be described next with reference to FIG. 9. FIG. 9 is a diagram illustrating the third biometric information C3. As stated above, the third biometric information C3 represents a pulse wave signal originating from a human pulse wave. In the present exemplary embodiment, conversion to the third biometric information C3 is computed by acquiring changes in luminance in a plurality of images taken during a given period of time and performing noise removal processing such as time filtering and image averaging as appropriate. In the present exemplary embodiment, as stated above, image information A, which is a plurality of images as described above, is converted to biometric information. In this case, the image acquisition device 130 preferably captures images with a period shorter than the period of a pulse wave. Further, the image acquisition device 130 preferably captures images in a time period equivalent to at least one period of a pulse wave. One period of a pulse wave is at least 0.4 seconds and at most 2 seconds. A plurality of images at any one of wavelengths in image information A or a plurality of images at a plurality of wavelengths in image information A may be used. Returning to FIG. 3, the description of the configuration of the biometric authentication apparatus 100 will be continued.

The reliability information acquisition unit 143 acquires authenticity information and liveness information in reliability information D on the basis of first biometric information C1, second biometric information C2 and third biometric information C3 acquired by the image-to-biometric-information conversion unit 141. The reliability information D will now be described.

In the present exemplary embodiment, the reliability information D includes authenticity information and liveness information. The authenticity information is information on which to base the determination as to whether an object under measurement is a human finger or a fake finger. For example, the authenticity information is information indicating the degree of matching or degree of correlation between first biometric information C1 and second biometric information C2; if the degree of matching is higher than a predetermined value or the degree of correlation is higher than a predetermined value, the reliability determination unit 144, which will be described later, determines that the object under measurement is authentic and not fake. For this purpose, the authentication information acquisition unit 142, which will be described later, acquires authentication information E. On the other hand, if the degree of matching is lower than the predetermined value or the degree of correlation is lower than the predetermined value, the reliability determination unit 144 determines that the object under measurement is fake and not authentic, and the authentication information acquisition unit 142, which will be described later, does not acquire authentication information E.

An example of the authenticity information in the reliability information D will now be described. First, the reliability information acquisition unit 143 performs a process for superimposing first biometric information C1 and second biometric information C2 on one another or calculating the correlation between first biometric information C1 and second biometric information C2. The authenticity information is based on the superimposed images. The reliability information acquisition unit 143 then extracts the degree of matching between the superimposed images or calculates a cross-correlation function between the superimposed images. The degree of matching is the number of match points, for example, and the higher the degree of matching, the likelier C1 and C2 are identical to each other. The cross-correlation function represents the similarity between C1 and C2 and can be calculated by convolution, if a result of a function arrangement is close to 1, there is a correlation; if a result for a function arrangement is close to 0, there is not a correlation. Accordingly, if the degree of matching is lower than a predetermined value or a value of the cross-correlation function is lower than a predetermined value, the reliability determination unit 144 determines that there is a significant difference between the first biometric information C1 and the second biometric information C2 and determines that the object under measurement is fake and not authentic. In this case, the reliability determination unit 144 determines that authentication information E cannot be acquired.

For example, superimposing first biometric information C1 and second biometric information C2 on one another normally shows a high degree of matching and almost all feature points can be extracted. Further, calculating the cross-correlation function between first biometric information C1 and second biometric information C2 yields a high value close to 1. Accordingly, in these cases, it is determined that the object under measurement is authentic and not fake. On the other hand, if there is foreign matter on the surface of the finger, superimposing first biometric information C1 and second biometric information C2 Will show that C1 and C2 do not match and feature points cannot be extracted in most portions. Further, calculating the cross-correlation function between first biometric information C1 and second biometric information C2 will yield a low value close to 0. Accordingly, it is determined that the object under measurement is fake and not authentic. In another example, if there is soil or the like in a portion of the surface of a finger, superimposing first biometric information C1 and second biometric information C2 will show a low degree of snatching in the portion and feature points cannot be extracted from the portion. Further, the value of the cross-correlation function between first biometric information C1 and second biometric information C2 in the portion will be lower than a predetermined value. However, if the degrees of matching in the other portions are higher than the predetermined value or if values of the cross-correlation function in the other portions are higher than the predetermined value, it is determined that the object under measurement is authentic.

An example in which the reliability information acquisition unit 143 acquires liveness information of reliability information D will be described. The reliability information acquisition unit 143 acquires an amplitude of third biometric information C3. If the amplitude of a pulse wave signal is smaller than a predetermined amplitude, the reliability determination unit 144 determines that the object under measurement is not a living body, i.e. dead and not alive or that the object under measurement is a fake.

The reliability determination unit 144 makes a determination as to whether biometric information is reliable on the basis of reliability information D acquired by the reliability information acquisition unit 143 as described above. If the degree of matching between images acquired by the reliability information acquisition unit 143 as described above is lower than a predetermined value or if the degree of correlation is lower than a predetermined value, the reliability determination unit 144 determines that there is a significant difference between first biometric information C1 and second biometric information C2 and determines that the object under measurement is fake and not authentic. If the amplitude of a pulse wave signal is smaller than a predetermined value, the reliability determination unit 144 determines that the object under measurement is not a living body, i.e. dead and not alive or that the object under measurement is a fake.

Figure 10:
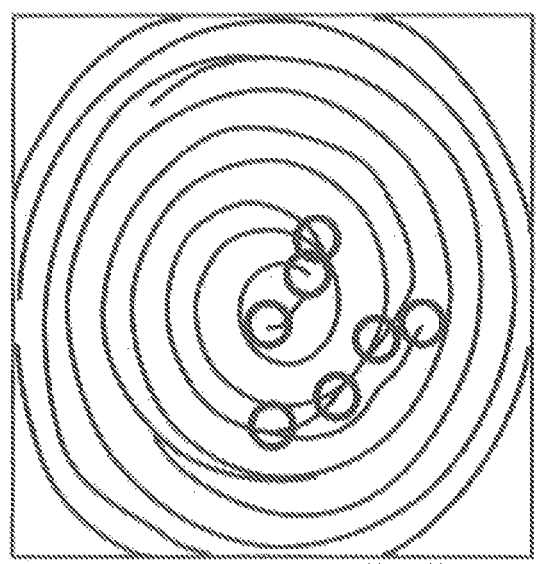
FIG. 10 is a diagram illustrating an example of authentication information E.

The computing device 140 includes an authentication information acquisition unit (authentication information acquisition means) 142 and a biometric authentication unit (biometric authentication means) 145. In addition to the image-to-biometric-information conversion unit 141, the reliability information acquisition unit 143 and the reliability determination unit 144 described above. The authentication information acquisition unit 142 acquires authentication information E on the basis of first biometric information C1 and second biometric information C2 resulting from conversion by the image-to-biometric-information conversion unit 141. The authentication information E will be described with reference to FIG. 10 first. In conjunction with, the description of the authentication information E, a method for acquiring the authentication information E will be described. FIG. 10 is a diagram illustrating an example of the authentication information E.

The authentication information E is information indicating the positions of feature points in a human fingerprint, such as the core, forks, ridge ends and deltas. First, information acquired when reliability information D has been acquired by the reliability information acquisition unit 143 using first biometric information C1 and second biometric information C2 is used as a prerequisite for the method for acquiring authentication information E. The information is image information resulting from superimposition of first biometric information C1 and second biometric information C2 or image information acquired by calculating the cross-correlation function as described above. Then the authentication information acquisition unit 142 extracts feature points from the image information resulting from the superimposition of the first biometric information C1 and the second biometric information C2 or from the image information acquired by calculating the cross-correlation function between the biometric information C1 and the second biometric information C2 and converts the feature points to coordinate data.

This enables the biometric authentication unit 145 to perform biometric authentication by determining whether or not the coordinate data, which is acquired authentication information E, matches coordinate data registered in advance, as will be described later. Note that the method for acquiring the authentication information E may be a feature point extraction method (a minutiae-based method). The method is a well-known technique and therefore the description of the method will be omitted. While the method for acquiring the authentication information E may be a feature point extraction method as stated above, other methods are not excluded and a pattern matching method may be used.

(Process Performed by the Biometric Authentication Apparatus 100)

Figure 11:
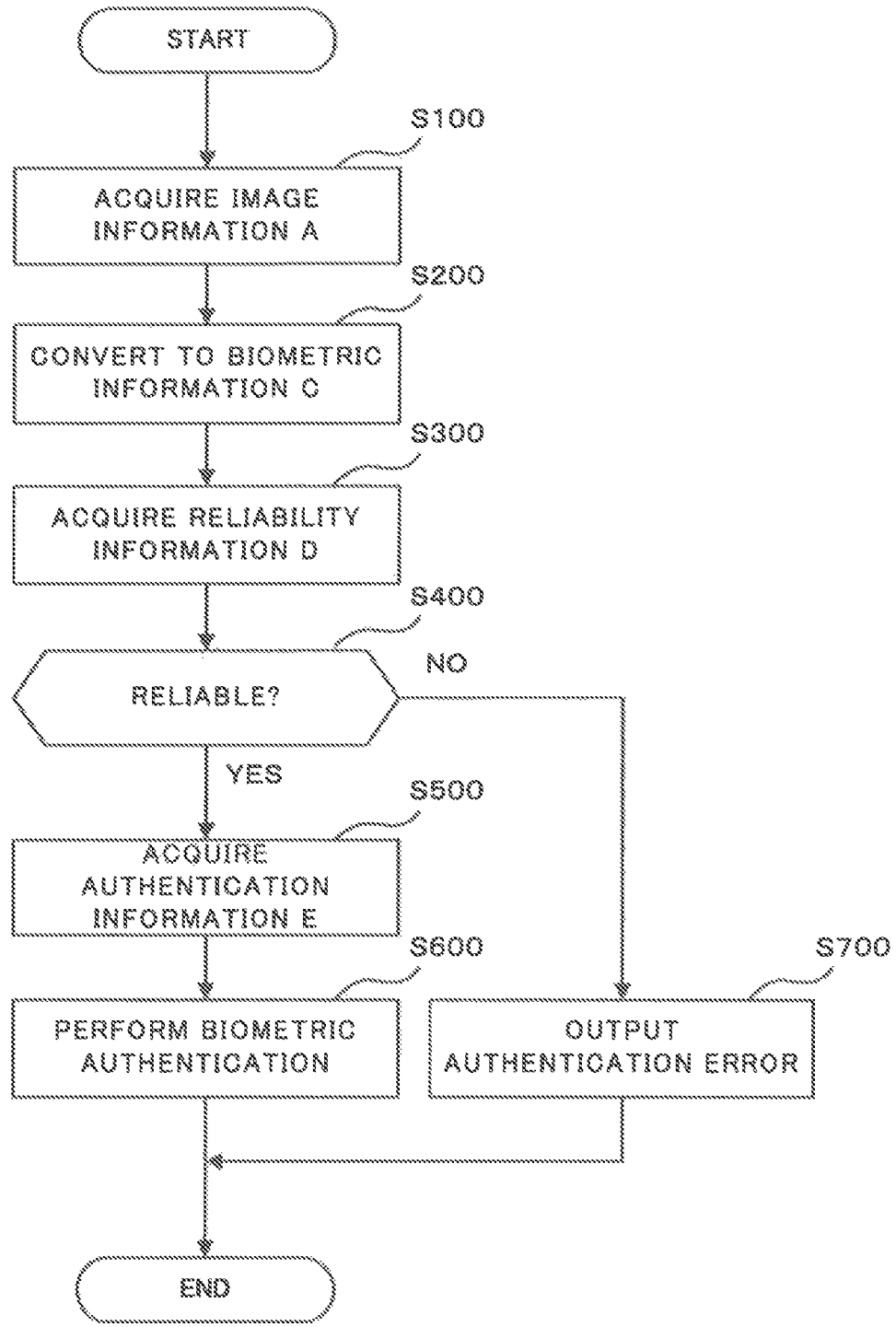
FIG. 11 is a flowchart of a process performed by the biometric authentication apparatus according to the alternative exemplary embodiment (the second exemplary embodiment) of the present invention.

A process performed by the biometric authentication apparatus 100 according to the present exemplary embodiment will be described next with reference to FIG. 11. FIG. 11 is a flowchart of a process performed by the biometric authentication apparatus 100 according to the present exemplary embodiment (the second exemplary embodiment).

In step S100 the image acquisition device 130 acquires image information A1, image information A2 and image information A3. The method for acquiring these pieces of image information A1 to A3 is as described above and therefore the description of the method will be omitted here.

In step S200, the computing device 140 converts the image information A1 to A3 to first biometric information C1, second biometric information C2 and third biometric information C3, respectively. The method for converting to the first to third biometric information C1 to C3 is as described above and therefore the description of the method will be omitted here.

In step S300, the computing device 140 acquires reliability information D. In this process, the computing device 140 acquires authenticity information and liveness information as the reliability information D. The methods for acquiring the authenticity information and liveness information are as described above and therefore the description of the methods will be omitted here.

In step S400, the computing device 140 makes a determination as to the reliability on the basis of the reliability information D acquired in step S300. Is this process, the computing device 140 uses authenticity information in the reliability information D to determine whether the degree of matching is higher than a predetermined value or determine whether the degree of correlation is higher than a predetermined value. Further, in this process, the computing device 140 uses liveness information in the reliability information D to determine whether the amplitude of a pulse wave signal is greater than a predetermined amplitude. In this process, if the computing device 140 determines, on the basis of the authenticity information in the reliability information D, that the degree of matching is higher than the predetermined value or the degree of correlation is higher than a predetermined value, the process proceeds to step S500. On the other hand, if the computing device 140 determines in this process that the degree of matching is lower than the predetermined value or the degree of correlation is lower than the predetermined value, the process proceeds to step S700. Likewise, in this process, if the computing device 140 determines, on the basis of the liveness information in the reliability information D, that the amplitude of the pulse wave signal is greater than the predetermined amplitude, the process proceeds to step S500. On the other hand, in this process, if the computing device 140 determines that the amplitude of the pulse wave signal is smaller than the predetermined amplitude, the process proceeds to step S700.

In step S500, the computing device 140 acquires authentication information E. The method for acquiring the authentication information E is as described above and therefore the description of the method will be omitted here.

In step S600, the computing device 140 refers to a database, not depicted, and compares the authentication information E acquired in step S300 with the data in the database, thereby performing biometric authentication. The database may be stored on a database server and may be connected to the computing device 140 through a network, not depicted. While the database is referred to in the present exemplary embodiment, other methods are not excluded. For example, an IC tag may be embedded in a passport or the like and biometric identification information may be stored in the IC tag. The passport may be presented and the biometric identification information in the passport may be compared with authentication information E acquired in step S300 described above, "IC" is an abbreviation for "Integrated Circuit".

In step S700, the computing device 140 outputs an authentication error and ends the current process without automatically performing authentication. The computing device 140 may provide a notification of the authentication error and the reason for the authentication error to a display unit, not depicted, a speaker, not depicted, or the like.

(Exemplary Applications)

Figure 12:
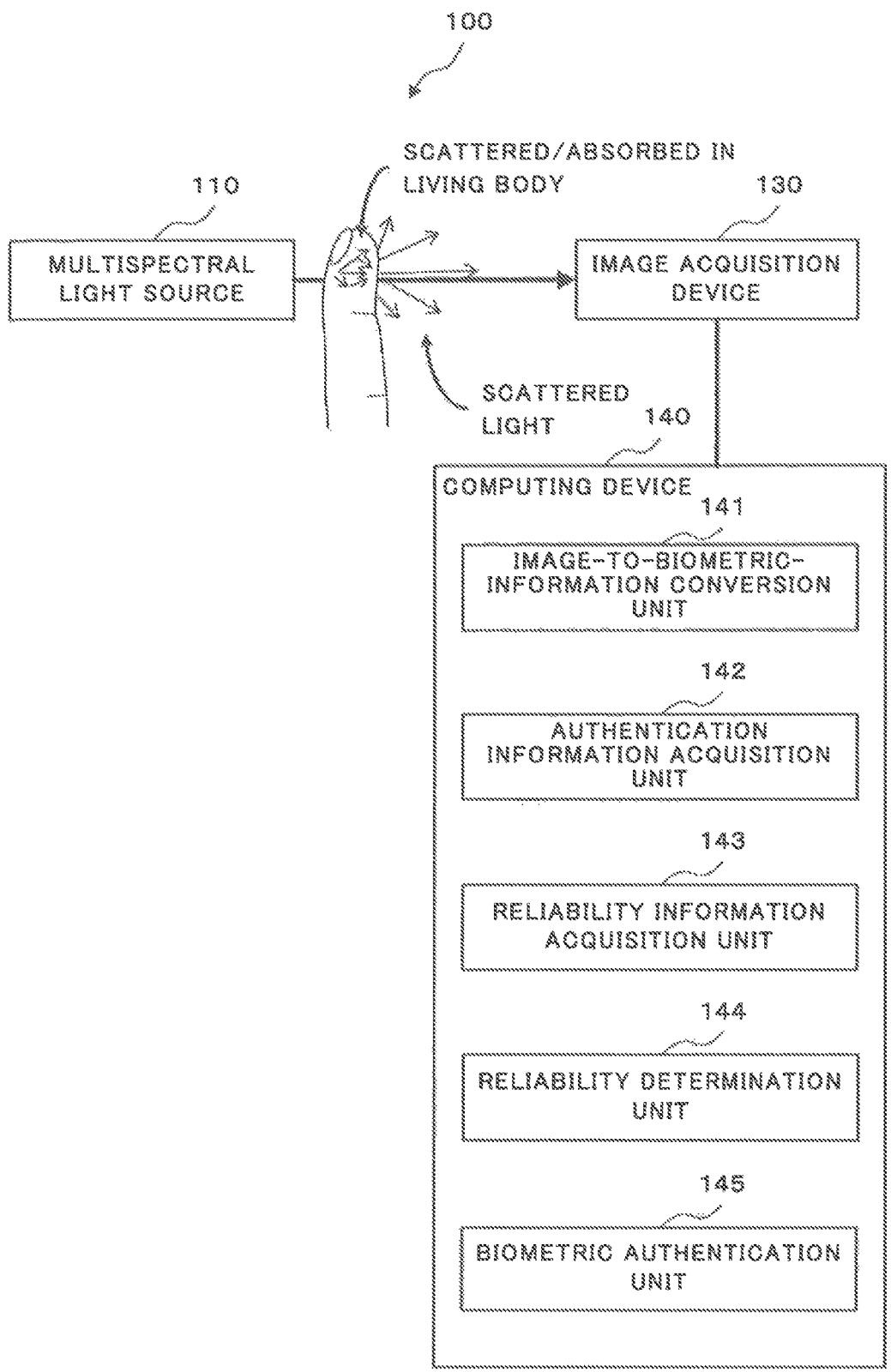
FIG. 12 is a diagram illustrating a first example use of the biometric authentication apparatus according to the alternative exemplary embodiment (the second exemplary embodiment) of the present invention.
Figure 13:
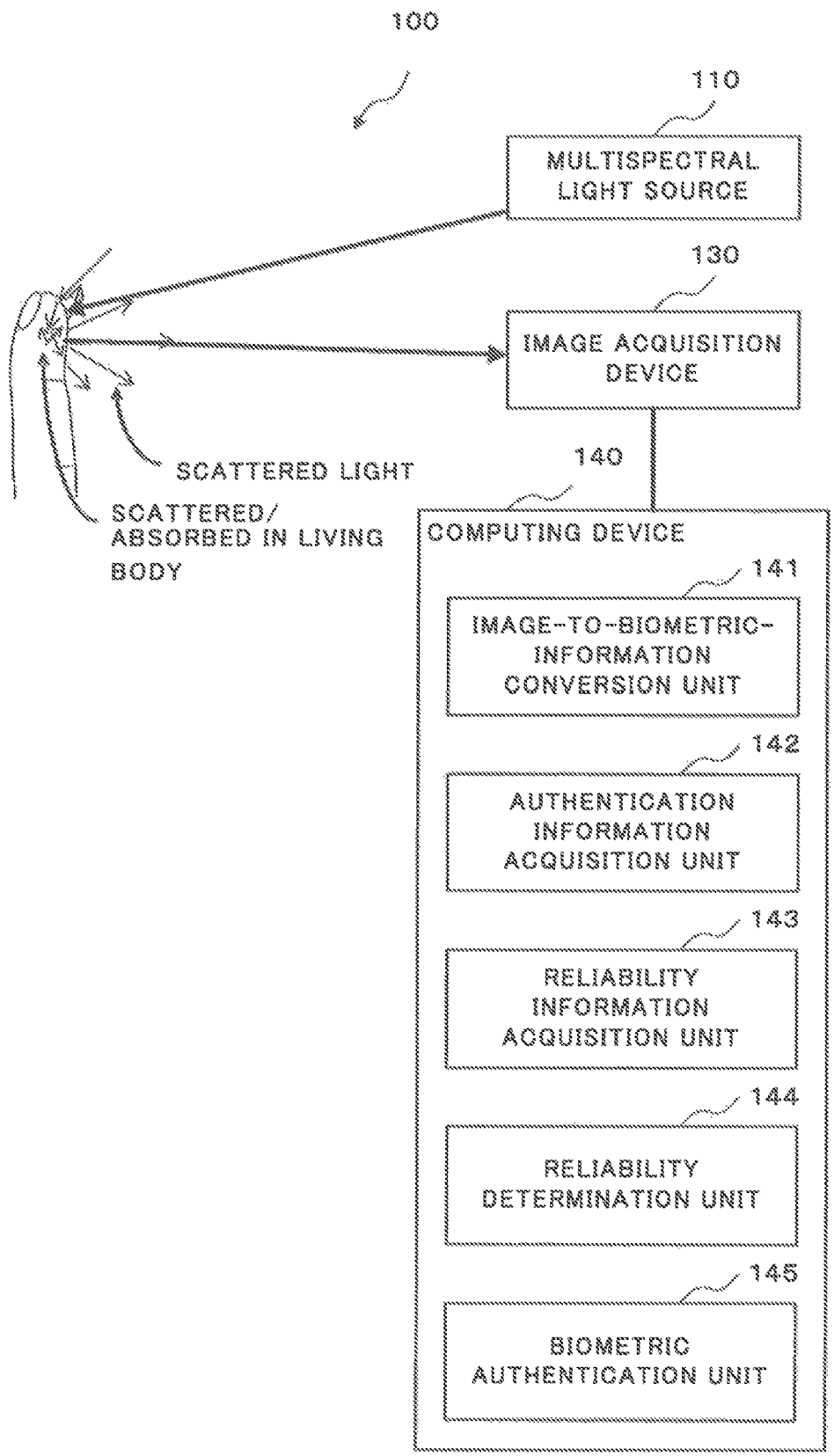
FIG. 13 is a diagram illustrating a second example use of the biometric authentication apparatus according to the alternative exemplary embodiment (the second exemplary embodiment) of the present invention.

Exemplary applications of the present exemplary embodiment (the second exemplary embodiment) will be described next with reference to FIGS. 12 and 13. FIG. 12 is a diagram illustrating a first exemplary application of the biometric authentication apparatus 100 according to the present exemplary embodiment (the second exemplary embodiment). FIG. 13 is a diagram illustrating a second exemplary application of the biometric authentication apparatus 100 according to the present exemplary embodiment (the second exemplary embodiment).

As illustrated in FIG. 12, when the biometric authentication apparatus 100 allows light irradiated from a multispectral light source 110 to pass through a human finger, the light is scattered or absorbed in the human finger and the image acquisition device 130 captures images of the scattered light. On the basis of the captured images, the computing device 140 in the biometric authentication apparatus 100 performs biometric authentication and reliability determination as described above.

In contrast, as illustrated in FIG. 13, when the biometric authentication apparatus 100 allows light irradiated from the multispectral light source 110 to be reflected, the light is reflected at the surface of the human finger or scattered or absorbed in the human finger. Images of the light scattered in the finger that is a part of the irradiated light are captured by the image acquisition device 130. On the basis of the captured images, the computing device 140 in the biometric authentication apparatus 100 performs biometric authentication and reliability determination as described above.

In this way, the present exemplary embodiment uses only optical devices in conversion to biometric information: the multispectral light source 110 irradiates a human finger with light and the image acquisition device 130 acquires a plurality of images at different wavelengths of the irradiated light. For this reason, for example, the present exemplary embodiment does not need to take into consideration interference between the frequency of ultrasound and the frequency of electromagnetic waves generated by an inverter installed in an air conditioner or the like and therefore can be introduced in a wide variety of facilities.

Further, in the present exemplary embodiment, reliability information is acquired on the basis of biometric information, determination is made as to whether biometric authentication, is reliable on the basis of the acquired reliability information, and thus it may be determined, for example, that a finger does not belong to a person to be authenticated but is a finger cut from another person. According to the present embodiment, this prevents biometric authentication of a finger cut from a person or the like from being performed, thereby improving the reliability of the biometric authentication. Thus, the present exemplary embodiment can be introduced in a wide variety of facilities and improve the reliability of biometric authentication to ensure a high level of security, as described above.

Moreover, in the biometric authentication apparatus 100 according to the present exemplary embodiment, the multispectral light source 110 can be disposed on the light transmission, side or on the light reflection side of a living body and can be located as desired in a facility that uses the biometric authentication apparatus 100. Thus, the biometric authentication apparatus 100 according to the present exemplary embodiment has broad utility.

Third Exemplary Embodiment

Figure 14:
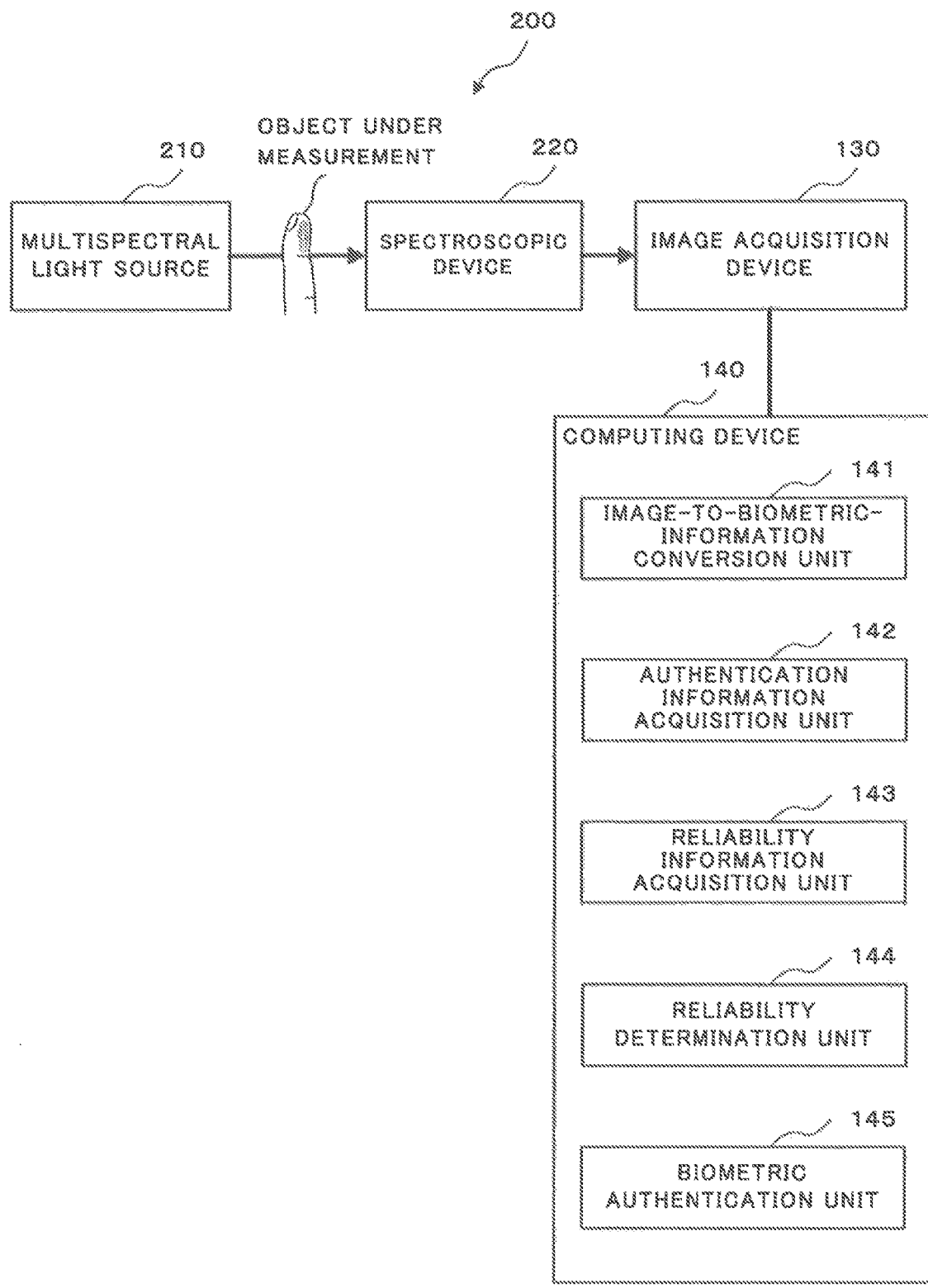
FIG. 14 is a configuration diagram illustrating a configuration of a biometric authentication apparatus according to another alternative exemplary embodiment (a third exemplary embodiment) of the present invention.

Another exemplary embodiment (a third exemplary embodiment) of the present invention will be described with reference to FIG. 14. FIG. 14 is a configuration diagram illustrating a configuration of a biometric authentication apparatus 200 according to the present exemplary embodiment (the third exemplary embodiment). The present exemplary embodiment differs from the second exemplary embodiment described above in that the present exemplary embodiment uses a white light source as the multispectral light source 210 and accordingly includes a spectroscopic device 220. The other components, the image acquisition device 130 and the computing device 140, are the same as those of the second exemplary embodiment. Therefore, in the following description of the present exemplary embodiment, the multispectral light source 210 and the spectroscopic device 220, which are different from the components of the second exemplary embodiment, will be described and the image acquisition device 130 and the computing device 140, which are the same components as those in the second exemplary embodiment, will be given the same reference numerals and the descriptions thereof will be omitted.

In the present exemplary embodiment, the multispectral light source 210 of the biometric authentication apparatus 200 is a white light source as mentioned above. The white light source is a light source that irradiates light whose spectrum contains components in different wavelength regions. Note that while the multispectral light source 210 is implemented by a white light source as stated above, the light source is not limited to this; for example, the multispectral light source 210 may be a fluorescent lamp, a halogen lamp, white LEDs, an incandescent light bulb or the like.

In the present exemplary embodiment, the role of the spectroscopic device 220 is to selectively extract a given wavelength from light irradiated from the multispectral light source 210. The spectroscopic device 220 in the present exemplary embodiment is implemented by a liquid-crystal bandpass filter, for example. The liquid-crystal bandpass filter changes a voltage to be applied to liquid crystal to control wavelengths to pass. While the spectroscopic device 220 is implemented by the liquid-crystal bandpass filter as mentioned above, the spectroscopic device 220 is not limited to this; for example, the spectroscopic device 220 may be implemented by a prism, a grating or a Fourier transform spectroscopic device.

The image acquisition device 130 of the biometric authentication apparatus 200 acquires image information A and the computing device 140 converts the acquired image information A to biometric information C. The biometric authentication apparatus 200 acquires reliability information D and authentication information E on the basis of the biometric information C resulting from the conversion. By using these items of information, the computing device 140 of the biometric authentication apparatus 200 performs biometric authentication and reliability determination.

In this way, the present exemplary embodiment uses only optical devices in conversion to biometric information: the multispectral light source 210 irradiates a human finger with light and the image acquisition device 130 acquires a plurality of images at different wavelengths of the irradiated light. For this reason, for example, the present exemplary embodiment does not need to take into consideration, interference between the frequency of ultrasound and the frequency of electromagnetic waves generated by an inverter installed in an air conditioner or the like and therefore ears be introduced in a wide variety of facilities.

Further, in the present exemplary embodiment, reliability information is acquired on the basis of biometric information, determination is made as to whether biometric authentication is reliable on the basis of the acquired reliability information. Thus, it may be determined, for example, that a finger does not belong to a person to be authenticated but is a finger cut from another person or a fake finger. In response to the determination, the present exemplary embodiment prevents biometric authentication of a finger cut from a person or the like from being automatically performed and provides a notification that the object under measurement can be a finger out from another person or a fake finger, thereby improving the reliability of the biometric authentication. Thus, the present exemplary embodiment can be introduced in a wide variety of facilities and improve the reliability of biometric authentication to ensure a high level of security, as stated above.

Moreover, since the spectroscopic device 220 of the biometric authentication apparatus 200 in the present exemplary embodiment is capable of selectively extracting a wavelength of light irradiated from a wavelength-invariable light source as described above, the biometric authentication device 200 is not limited to the use with a wavelength-variable light source but has broad utility.

Fourth Exemplary Embodiment

Another exemplary embodiment (a fourth exemplary embodiment) of the present invention will be described with reference to FIG. 1. As illustrated in FIG. 1, a biometric authentication apparatus 10' according to the present exemplary embodiment includes a illumination unit 11, an image acquisition unit 13, an image-to-biometric-information conversion unit 14 and a biometric authentication unit 16.

The illumination unit 11 irradiates a human finger with light. The image acquisition unit 13 receives light scattered at the human finger that is a part of the light with which the human finger is irradiated by the illumination unit 11 and converts the received light to luminance information according to the intensity of the light to acquire a plurality of images that represent changes in luminance. The image-to-biometric-information conversion unit 14 converts the plurality images acquired by the image acquisition unit 13 to biometric information indicating a pulse wave in the human finger. If the amplitude of a pulse wave signal, which is biometric information resulting from, conversion, by the image-to-biometric-information conversion unit 14, is greater than a predetermined threshold, the biometric authentication unit 16 automatically performs biometric authentication.

Thus, the present exemplary embodiment can be introduced in a wide variety of facilities and improve the reliability of biometric authentication to ensure a high level of security.

As above, the present invention has been described based on the exemplary embodiments. An exemplary embodiment is just an illustration, and various kinds of changes, addition or subtraction and combinations may be added to each of the above-mentioned exemplary embodiments unless it deviates from the main points of the present invention. It is understood by a person skilled in the art that modification made by adding such changes, addition/subtraction and combinations are also included in the scope of the present invention.

While the present invention has been described with reference to exemplary embodiments thereof, the present invention is not limited to the exemplary embodiments described above. Various modifications that can be understood by a person skilled in the art can be made to the configurations and details of the present invention within the scope of the present invention.

This application is based upon and claims the benefit of priority from the prior Japanese Patent Application No. 2014-219806, filed on Oct. 29, 2014, the entire disclosure of which is incorporated herein.

REFERENCE SIGNS LIST

10 Biometric authentication apparatus
11 Illumination unit
13 Image acquisition unit
14 Reliability determination unit
16 Biometric authentication unit

The invention claimed is:

1. A biometric authentication apparatus comprising:
    a memory storing instructions; and
    one or more processors coupled to the memory and configured to execute the instructions to:
    irradiate a human finger with light generated by a light source;
    acquire, via an image acquisition device, a plurality of images indicating changes in luminance by receiving light scattered at the human finger that is a part of the light with which the human finger is irradiated and converting the received light to luminance information according to the intensity of the received light;
    convert the acquired plurality of images to biometric information indicating a pulse wave in the human finger; and
    perform automatically biometric authentication when the amplitude of a pulse wave signal is greater than a predetermined threshold, the pulse wave signal being the biometric information resulting from conversion.

2. The biometric authentication apparatus according to claim 1, wherein the one or more processors are further configured to execute the instructions to:
    irradiate light of different wavelengths;
    acquire each of images at different wavelengths of the irradiated light;
    convert an image at a first wavelength among the acquired images at the different wavelengths to first biometric information representing a fingerprint image of the human finger;

convert an image at a second wavelength different from the first wavelength to second biometric information relating to a fingerprint image of the human finger; and perform automatically biometric authentication when the degree of matching between fingerprint images which are the first biometric information and the second biometric information resulting from the conversion is high.

3. The biometric authentication apparatus according claim 2, wherein the one or more processors are further configured to execute the instructions to automatically perform biometric authentication by:

referring to a database stored in advance; and comparing the fingerprint images which are the first biometric information and the second biometric information with the referred database.

4. The biometric authentication apparatus according to claim 1, wherein the one or more processors are further configured to execute the instructions to:

switch a wavelength of light being irradiated as desired.

5. The biometric authentication apparatus according to claim 1, wherein the one or more processors are further configured to execute the instructions to:

extract selectively white light of a predetermined wavelength.

6. The biometric authentication apparatus according to claim 1, wherein the one or more processors are further configured to execute the instructions to:

notify that the amplitude of a pulse wave signal, the pulse wave signal being the converted biometric information, is smaller than the predetermined threshold without automatically performing biometric authentication, when the amplitude of the pulse wave signal is smaller than the predetermined threshold.

7. A biometric authentication method comprising:

irradiating a human finger with light;

when light scattered at the human finger that is a part of the irradiated light is received, converting the received light to luminance information according to the intensity of the light to acquire a plurality of images indicating levels of luminance;

converting the plurality of acquired images to biometric information indicating a pulse wave in the human finger; and when the amplitude of a pulse wave signal which is the biometric information resulting from the conversion is greater than a predetermined threshold, automatically performing biometric authentication.

8. A biometric authentication method comprising:

irradiating a human finger with light of different wavelengths;

acquiring an image at each of the different wavelengths of the irradiated light;

converting an image at a first wavelength among the acquired images to first biometric information representing a fingerprint image of the human finger and converting an image at a second wavelength different from the first wavelength to second biometric information representing a fingerprint image of the human finger; and when the degree of matching between the fingerprint images which are the first biometric information and the second biometric information resulting from the conversion is high, automatically performing biometric authentication.

* * * * *